United States Patent
Yamamoto (10) Patent No.: US 8,216,410 B2
(45) Date of Patent: Jul. 10, 2012

(54) MANUFACTURING APPARATUS OF ABSORBENT ARTICLE AND MANUFACTURING METHOD OF ABSORBENT ARTICLE

(75) Inventor: Hiroki Yamamoto, Kanonji (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 12/943,041

(22) Filed: Nov. 10, 2010

(65) Prior Publication Data

US 2011/0057012 A1    Mar. 10, 2011

Related U.S. Application Data (62) Division of application No. 12/390,027, filed on Feb. 20, 2009.

(30) Foreign Application Priority Data

Nov. 11, 2008    (JP) ................................. 2008-289308

(51) Int. Cl.
*B32B 37/14*    (2006.01)
(52) U.S. Cl. ........ 156/176; 156/160; 156/276; 156/229; 156/440
(58) Field of Classification Search .................. 156/176, 156/276, 229
See application file for complete search history.

(56) References Cited

U.S. PATENT DOCUMENTS

| | | | |
|---|---|---|---|
| 5,389,173 A | * | 2/1995 | Merkatoris et al. ........... 156/164 |
| 6,585,841 B1 | * | 7/2003 | Popp et al. ..................... 156/161 |
| 2006/0185135 A1 | * | 8/2006 | Yamamoto et al. ............. 28/116 |

FOREIGN PATENT DOCUMENTS

| | | |
|---|---|---|
| JP | 03-033201 | 2/1991 |
| JP | 2006-141642 | 6/2006 |

* cited by examiner

*Primary Examiner* — Khanh P Nguyen
*Assistant Examiner* — Margaret Squalls
(74) *Attorney, Agent, or Firm* — Lowe, Hauptman, Ham & Berner, LLP (57) ABSTRACT

Included is a tip end portion being a feeding position from which a filiform elastic member is fed. By an arm member guiding the elastic member, the tip end portion is alternately moved in a first direction and a second direction, and thereby the elastic member is brought into contact with the web and is arranged in a gather waveform. Here, the first direction is from the center portion of a web being conveyed in a predetermined direction and having sequentially-arranged component parts forming one part of an absorbent article, to a first end portion in a cross direction crossing with a conveyance direction, and the second direction is from the center to a second end portion which is an end portion opposite to the first end portion. At this time, in a planar view of a composite web, when a nip point exceeds a position where an angle between the conveyance direction and a tangent to the gather waveform is largest, a distance between the tip end portion and the nip point is largest.

10 Claims, 6 Drawing Sheets

MANUFACTURING APPARATUS OF ABSORBENT ARTICLE AND MANUFACTURING METHOD OF ABSORBENT ARTICLE

RELATED APPLICATIONS

The present application is a divisional of U.S. application Ser. No. 12/390,027, filed Feb. 20, 2009 is based on, and claims priority from, Japanese Application Number 2008-289308, filed Nov. 11, 2008, the disclosure of which is hereby incorporated by reference herein in its entirety.

BACKGROUND OF THE INVENTION

1. Field of the Invention

The present invention relates to a manufacturing apparatus of an absorbent article and a manufacturing method of an absorbent article for arranging an elastic member on a web by using a guide unit guiding the elastic member, the web being conveyed in a predetermined direction in a state in which components forming one part of the absorbent article are sequentially arranged.

2. Description of the Related Art

Conventionally, the manufacturing process of an absorbent article such as a disposable diaper widely uses a method of arranging a filiform elastic member (rubber) having stretching properties in positions corresponding to leg circumferential regions and a crotch region, in order to improve the fittingness of the leg circumferential regions and the crotch region to a target wearing the article (for example, a human body).

Specifically, in the manufacturing process, a filiform elastic member is arranged in a waveform on a web in which components of absorbent articles, such as back sheets or absorbent sheets, are sequentially arranged. That is, the filiform elastic member is arranged in a waveform on a crosswise-flow web in which the longitudinal direction of the absorbent article is arranged in a cross direction (CD) crossing a conveyance direction (Machine Direction(MD)) of the web. Accordingly, the absorbent articles each provided with gathers corresponding to the shapes of the leg circumferential regions and the crotch region can be continuously manufactured.

As such a method of arranging a filiform elastic member in a waveform on a web being conveyed, known is a method in which a guide member guiding the elastic member to a feeding position on the web is driven by a cam (for example, see Japanese Unexamined Patent Application Publication No. H3-33201 (page 4, FIGS. 6 and 7)).

In addition, known is a method in which a guide member guiding an elastic member to a feeding position on a web is reciprocated in cross directions crossing a conveyance direction of the web (for example, Japanese Patent Application Publication No. 2006-141642 (page 10, FIG. 1)).

In this regard, the feeding position of the elastic member from the guide member may be positioned exactly at a nip point where an elastic member and a web are brought into contact with each other by being together held between press rollers provided above and under the web, and this positioning may be made by bringing the guide member into direct contact with the nip point. In fact, however, such positioning is not practical because of the layout of the apparatus. For this reason, designing a profile of an apparatus that moves a guide member is required to consider this distance.

However, the above-described conventional manufacturing apparatus of an absorbent article has the following problem. Specifically, this problem is that the profile of a device such as a cam has to be precisely designed in consideration of a distance between a nip point and a feeding position in order to accurately arrange an elastic member in a desired position on a web which is being conveyed at high speed.

SUMMARY OF THE INVENTION

The present invention has been made in light of the foregoing situation. Accordingly, an object of the present invention is to provide a manufacturing apparatus of an absorbent article and a manufacturing method of an absorbent article which are capable of arranging an elastic member in a desired position on a web which is being conveyed at high speed without requiring precise profile designing.

To solve the above-described problem, the present invention includes the following aspects. Firstly, a first aspect of the present invention provides a manufacturing apparatus (elastic member fixing apparatus 100) of an absorbent article in which, with a guide unit (arm member 220) including a feeding portion (tip end portion 222) from which an elastic member (elastic member 6') is fed and guiding the elastic member, the feeding portion is moved alternately in a first direction (first direction Da) and a second direction (second direction Db) so that the elastic member is brought into contact with a web and is arranged in a predetermined waveform (gather waveform), the web (second web 7B or third web 7C) being conveyed in a predetermined direction in a state in which components forming one part of the absorbent article (absorbent article 1) are sequentially arranged, the first direction directing from a center portion of the web to a first end portion (first end portion 7a) in a cross direction (cross direction CD) crossing the predetermined direction (conveyance direction MD), and the second direction directing from the center portion to a second end portion (second end portion 7b) that is an end portion opposite to the first end portion. In the manufacturing apparatus, in a planar view of the web, when a nip point (N1, N2) at which the elastic member comes in contact with the web exceeds a position in the predetermined waveform where an angle (angle θ, φ) between the predetermined direction and a tangent to the predetermined waveform is largest, a distance (feeding distance LN1, LN2) between the feeding portion and the nip point is largest.

The aspect of the present invention can provide a manufacturing apparatus of an absorbent article and a manufacturing method of an absorbent article, in which an elastic member can be easily arranged along a certain waveform determined in advance in a desired position on a web which is being conveyed at high speed.

DESCRIPTION OF THE PREFERRED EMBODIMENT

A manufacturing method of an absorbent article according to the present invention will be described below by referring to the drawings. Specifically, the description will be given of the following points: (1) Configuration of Absorbent Article, (2) Manufacturing Method of Absorbent Article, (3) Configuration of Elastic Member Fixing Apparatus, (4) Configuration of Shaking Guide Mechanism, (5) Operation of Elastic Member Fixing Apparatus, (6) Advantages and Effects, and (7) Other Embodiments.

In the following description of the drawings, same or similar reference symbols are given to denote same or similar portions. However, it should be noted that the drawings are schematic and ratios of dimensions and the like are different from actual ones.

Therefore, specific dimensions and the like should be determined by taking into consideration the following description. Moreover, as a matter of course, also among the drawings, there are included portions in which dimensional relationships and ratios are different from each other.

(1) Configuration of Absorbent Article

Figure 1:
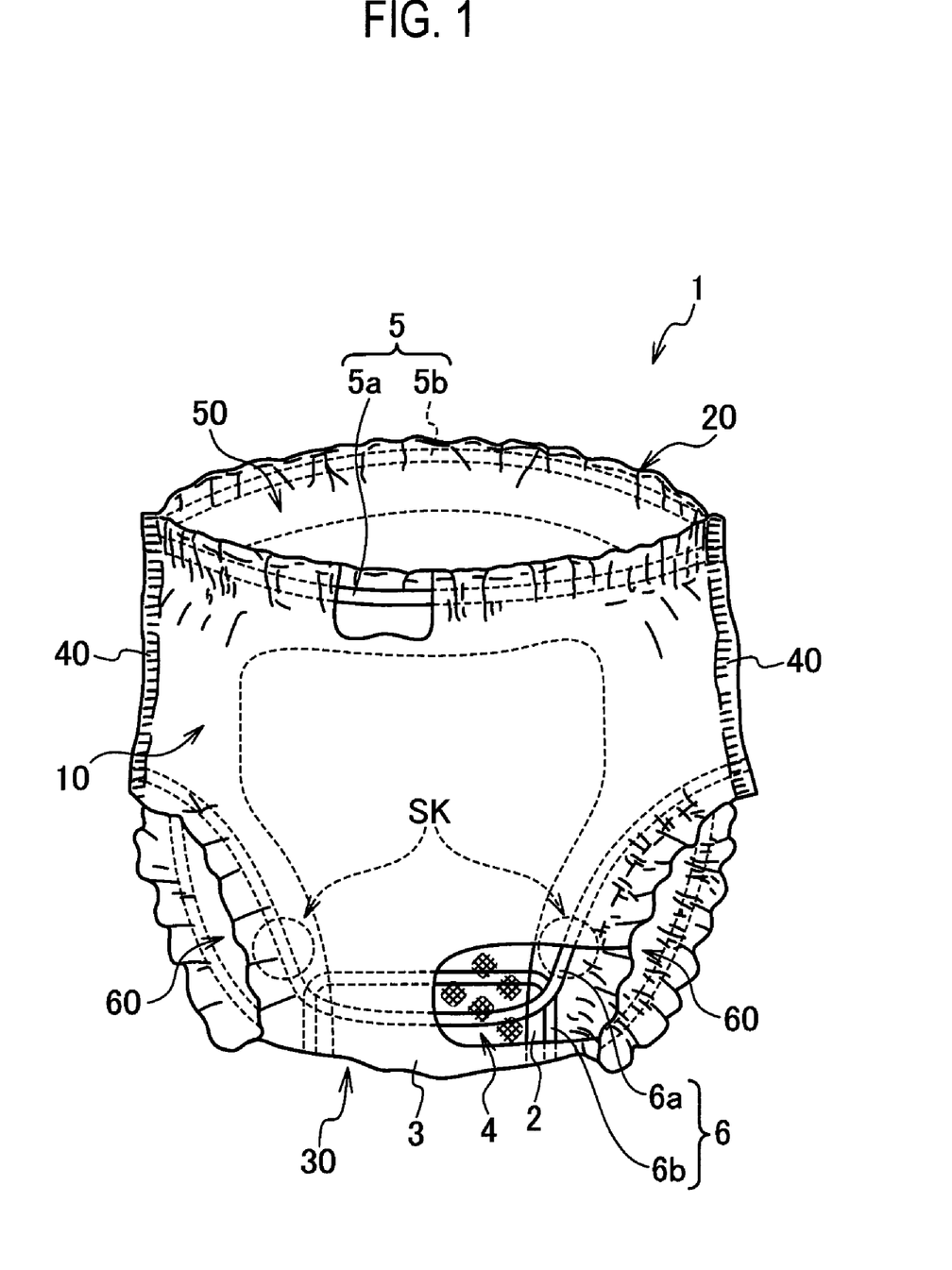
FIG. 1 is a perspective view showing an absorbent article according to the present embodiment.

Firstly, a configuration of an absorbent article according to the present embodiment will be described by referring to the drawings. FIG. 1 is a perspective view showing an absorbent article according to the present embodiment. In the present embodiment, an absorbent article 1 is a disposable diaper for adults.

As shown in FIG. 1, the absorbent article 1 is mainly formed of a liquid permeable front sheet 2 which comes in contact with a skin of a target wearing the article (hereinafter, a wearer), a back sheet 3 provided at the outer side of the front sheet 2, and an absorber 4 which is provided between the front sheet 2 and the back sheet 3, and absorbs dejecta from the wearer.

In addition, a liquid impermeable waterproof sheet (unillustrated) is provided between the back sheet 3 and the absorber 4. That is, the absorber 4 is provided between the front sheet 2 and the waterproof sheet.

As the front sheet 2, employed is a nonwoven fabric, a perforated plastic film, or the like. As the back sheet 3, employed is a nonwoven fabric. As the absorber 4, employed is ground pulp, a mixture of ground pulp and high absorbent polymer particles, or the like. As the waterproof sheet, employed is a plastic, a nonwoven fabric, a mixed sheet of a plastic film and a nonwoven fabric, or the like.

The absorbent article 1 has a front waistline region 10 corresponding to a front waistline of the wearer, a back waistline region 20 corresponding to a back waistline of the wearer, and a crotch region 30 corresponding to a crotch of the wearer.

The front waistline region 10 and the back waistline region 20 are integrated by connecting portions 40. A waist gather 5 made of a filiform rubber or the like having stretching properties is provided at the peripheries of the front waistline region 10 and the back waistline region 20. The waist gather 5 is formed of a front waist gather 5a positioned in the front waistline region 10 and a back waist gather 5b positioned in the back waistline region 20. A waistline opening region 50 is formed between the front waist gather 5a and the back waistline gather 5b.

The front waistline region 10 and the back waistline region 20 have stretching properties in a conveyance direction MD (MD direction) of a first web 7A forming the front sheet 2 and a second web 7B (see, FIG. 2) forming the back sheet 3. For example, the front waistline region 10 and the back waistline region 20 may be elastic in the conveyance direction MD by providing the waist gather 5 or may be elastic in the conveyance direction MD by forming the front waistline region 10 and the back waistline region 20 themselves with elastic sheets.

The crotch region 30 is provided between the front waistline region 10 and the back waistline region 20. Leg gathers 6, each formed of a filiform rubber having stretching properties or the like, are formed on both sides of the crotch region 30. The leg gather 6 is formed of a front leg gather 6a positioned closer to the front waistline region 10 and aback leg gather 6b positioned closer to the back waistline region 20. Leg circumferential opening regions 60 are formed at portions which are between the front leg gather 6a and the back leg gather 6b and on the both sides of the crotch region 30.

The crotch region 30 is elastic in the cross direction CD (CD direction) crossing the conveyance direction MD. For example, the crotch region 30 may be elastic in the cross direction CD by providing the leg gather 6 therein or may be elastic in the cross direction CD by forming the crotch region 30 itself with an elastic sheet.

Regions Sk shown in FIG. 1 show positions corresponding to inguinal regions of the wearer when the wearer wears the diaper. A method of arranging the front leg gather 6a in the regions Sk will be described in (5) Operation of Elastic Member Fixing Apparatus.

(2) Manufacturing Method of Absorbent Article

Figure 2:
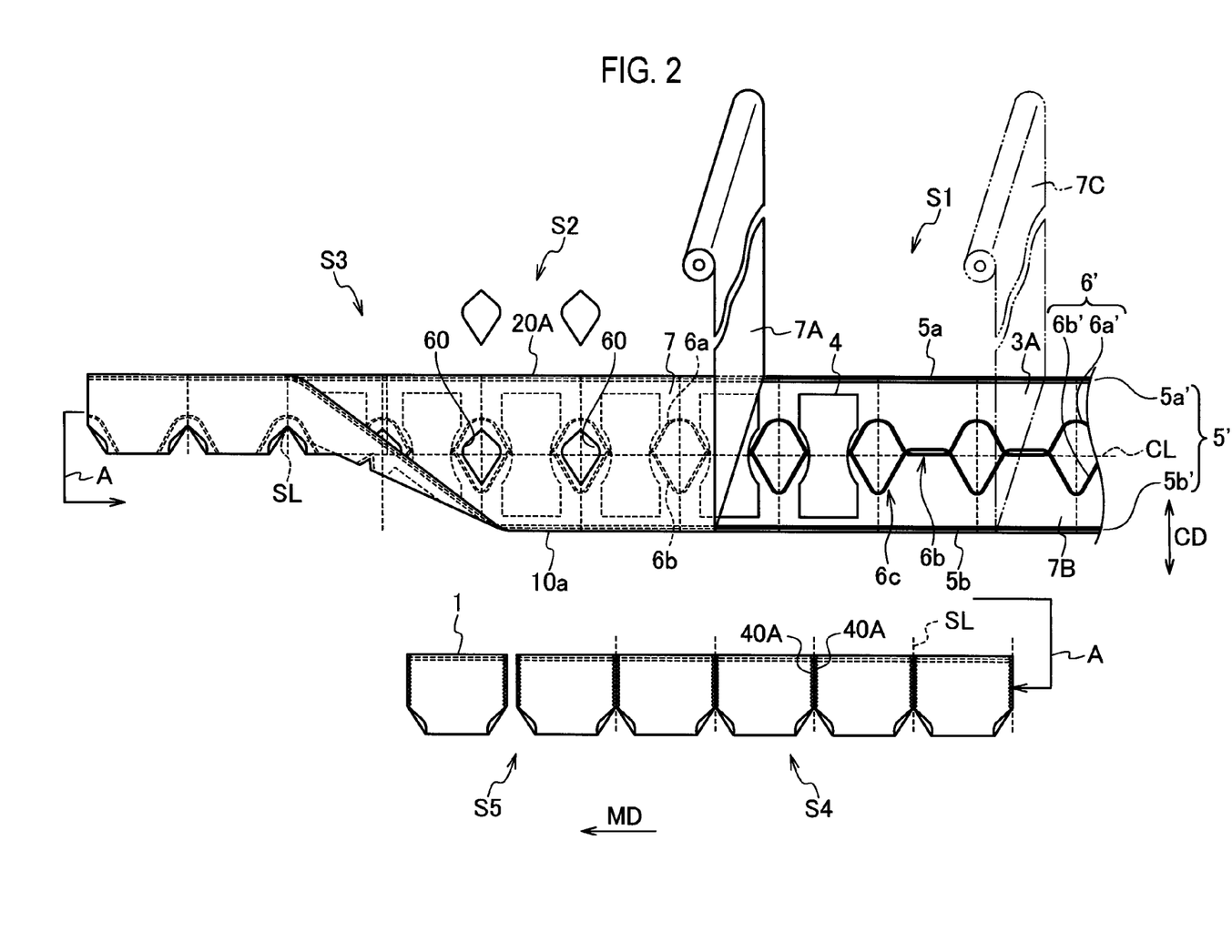
FIG. 2 is a view for illustrating one part of a manufacturing method of an absorbent article according to the present embodiment.

Next, a configuration of a manufacturing method of an absorbent article according to the present embodiment will be described by referring to the drawings. FIG. 2 is a view for illustrating a part of a manufacturing method of an absorbent article according to the present embodiment.

As shown in FIG. 2, the manufacturing method of an absorbent article includes at least a component mounting process, a leg circumference forming process, a folding process, a connecting process, and a cutting process. Note that processes of conveying webs in the conveyance direction MD (predetermined direction) are included between the individual processes by using an unillustrated conveyance apparatus (for example, a belt conveyance apparatus). The webs conveyed here are the liquid permeable first web 7A used to form the front sheet 2, the liquid impermeable second web 7B used to form the back sheet 3, and a third web 7C which is of the same material as that of the second web 7B and used to form the back sheet 3.

(2-1) Component Mounting Process

In the component mounting process S1, components constituting the absorbent article 1, such as the elastic member, the third web 7C, the waterproof sheet (unillustrated), and the absorber 4, are mounted on the second web 7B.

Specifically, firstly, the elastic member 5' forming the waist gather 5 in a stretched state is linearly mounted in the positions corresponding to the front waistline region 10 and the back waistline region 20 on the second web 7B. That is, the elastic member 5a' forming the front waist gather 5a and the elastic member 5b' forming the back waist gather 5b are mounted in the positions corresponding to the front waistline region 10 and the back waistline region 20 on the second web 7B. With this configuration, the waist gather 5 (the front waistline gather 5a and the back waist gather 5b) is formed in the positions corresponding to the front waistline region 10 and the back waistline region 20 on the second web 7B.

Secondly, the third web 7C is mounted on the second web 7B. At this time, the elastic member 6' forming the leg gather in the stretched state is arranged in the position corresponding to the crotch region 30 on the second web 7B and the third web 7C while swinging at a predetermined cycle in the cross direction CD. Then, the elastic member 6' is held between the second web 7B and the third web 7C to form the leg gather 6 (the front leg gather 6*a* and the back leg gather 6*b*).

Note that the second web 7B and the third web 7C which hold the elastic member 6' therebetween are pressed by an upper press roller 130A and a lower press roller 130B which will be described later.

The elastic member 6*a*' forming the front leg gather 6*a* and the elastic member 6*b*' forming the back leg gather 6*b* form a large ring portion 6C and a small ring portion 6*d* which has a smaller size in the cross direction CD than that of the large ring portion 6*c*.

As described above, after arranging the elastic member 6' on the second web 7B and the third web 7C, the second web 7B and the third web 7C are pressed by the upper press roller 130A and the lower press roller 130B. At this time, if a position in which the small ring portion 6*d* is designed to be formed is not pressed, the elastic member 6' is not fixed in the designed position on the web. The elastic member 6' is arranged in the stretched state, so that it contracts in the position where the elastic member 6' is not fixed on the web and thus forms a substantially straight line from a predetermined arranged shape. In this manner, the small ring portion 6*d* is formed.

The same holds for a case where an adhesive is not applied to the designed position. In the position where the adhesive is not designed to be applied, the elastic member 6' is not fixed on the web. Accordingly, the small ring portion 6*d* can be similarly formed.

Thirdly, the waterproof sheet (unillustrated) and the absorber 4 are mounted on the second web 7B and the third web 7C with the elastic member 6' being held therebetween so as to be uniformly spaced in the conveyance direction MD. The waterproof sheet may be mounted on the second web 7B and the third web 7C in a state being connected with the absorber 4 in advance, or may be mounted on the second web 7B and the third web 7C in a state being separated from the absorber 4.

Fourthly, the first web 7A forming the front sheet 2 overlaps the second web 7B and the third web 7C on which the components forming the absorbent article 1 are mounted.

Note that, the component mounting process S1 does not necessarily have to be performed in the order of the first step to the fourth step. The order may be changed if needed.

(2-2) Leg Circumference Forming Process

In the leg circumference forming process S2, after the component mounting process S1, an inner circumferential side of the large ring portion 6*c* is cut out on the second web 7B and the first web 7A with the components being held therebetween (hereinafter, a composite web 7) to form the leg circumference opening region 60 (so-called, a leg hole).

(2-3) Folding Process

In the folding process S3, after the leg circumference forming process S2, the composite web 7 is folded in two along the center line CL which passes through the center of the composite web 7 in the cross direction CD and extends in the conveyance direction MD. That is, a side edge 10A of the composite web 7 corresponding to the front waistline region 10 and a side edge 20A of the composite web 7 corresponding to the back waistline region 20 overlap each other being flush with each other.

(2-4) Connecting Process

In the connecting process S4, after the folding process S3, predetermined regions 40A corresponding to the connecting portions 40 of the absorbent article are connected with supersonic treatment or heat treatment. The predetermined regions 40A show both sides of a virtual line SL in the conveyance direction MD, which extends in the cross direction CD and shows a position designed to be cut.

(2-5) Cutting Process

In the cutting process S5, after the connecting process S4, the composite web 7 with the predetermined regions 40A connected is cut along the virtual line SL. In doing so, the absorbent article 1 is formed.

(3) Configuration of Elastic Member Fixing Apparatus

Figure 3:
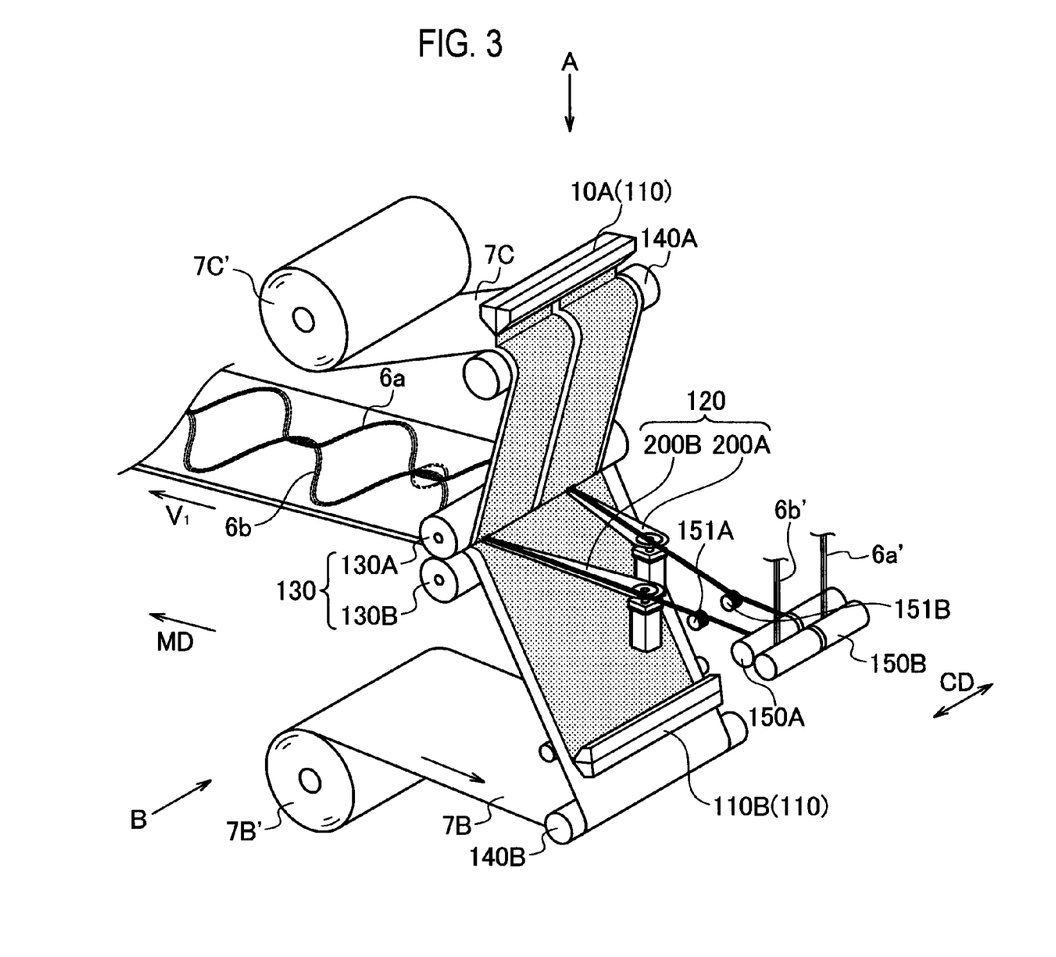
FIG. 3 is a perspective view showing an elastic member fixing apparatus according to the present embodiment.
Figure 4:
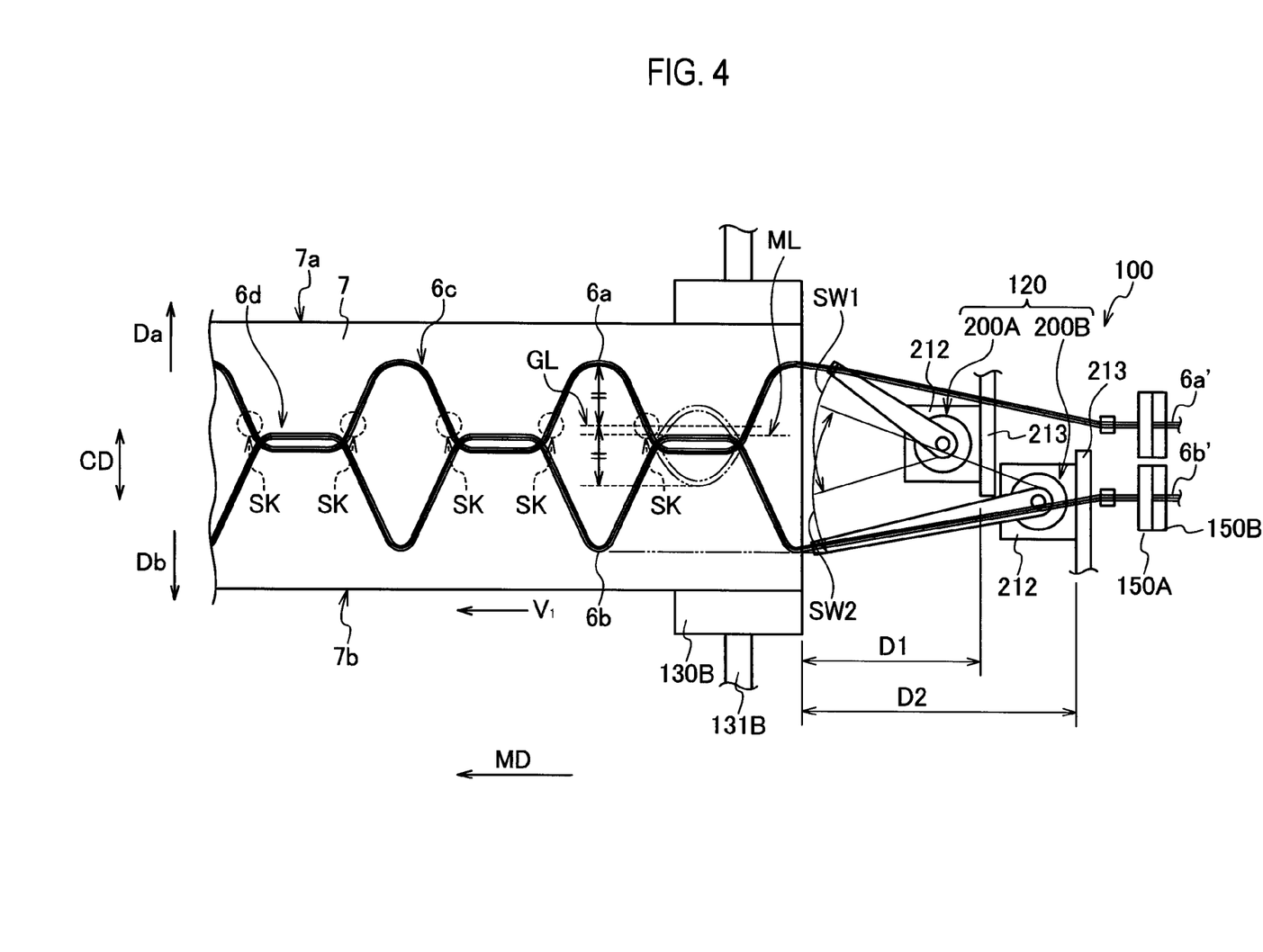
FIG. 4 is a top view (a view seen in the direction of the arrow A in FIG. 3) showing the elastic member fixing apparatus according to the present embodiment.
Figure 5:
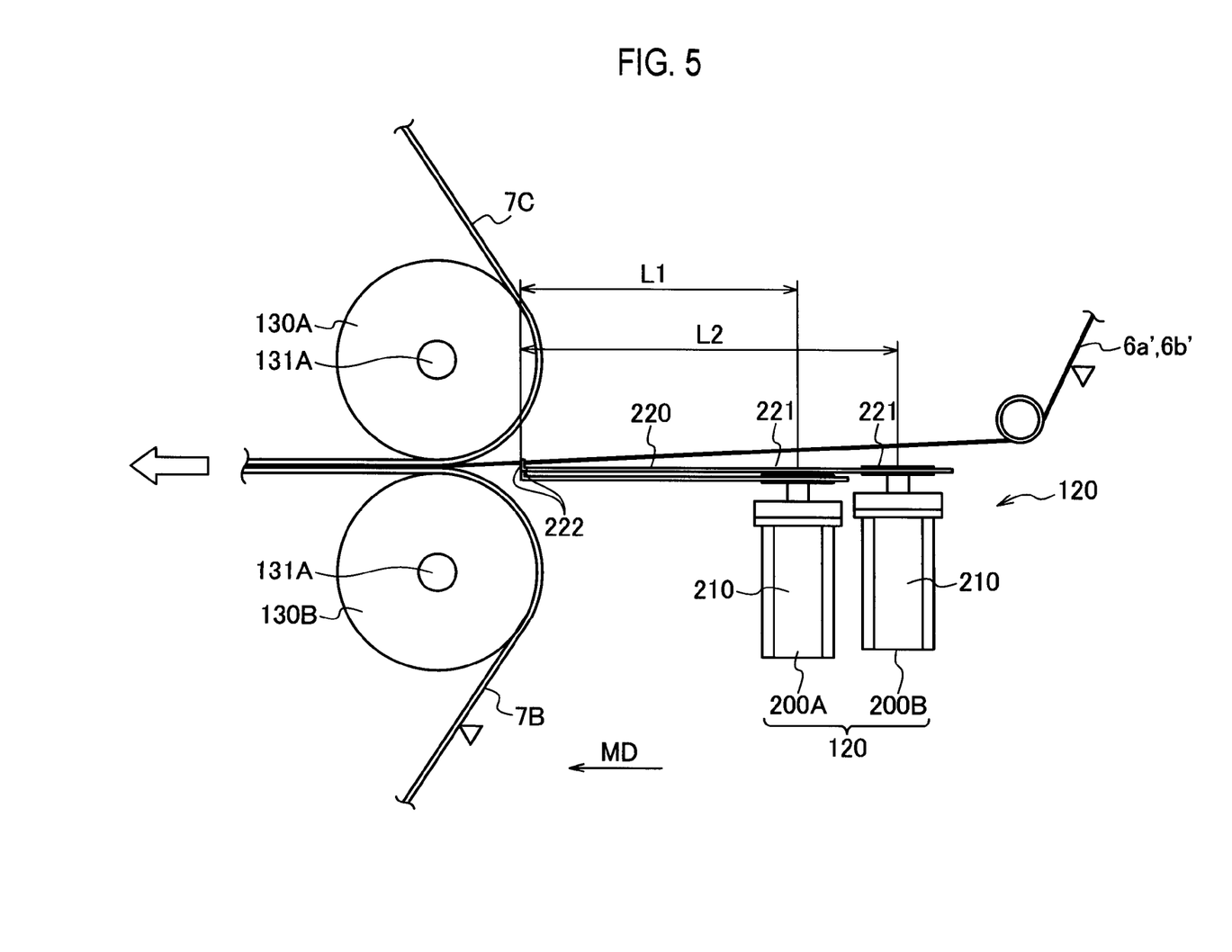
FIG. 5 is a side view (a view seen in the direction of the arrow B in FIG. 3) showing the elastic member fixing apparatus according to the present embodiment.

Next, the configuration of an elastic member fixing apparatus (manufacturing apparatus of an absorbent article) which is used in the above-described component mounting process will be described by referring to the drawings. FIG. 3 is a perspective view showing an elastic member fixing apparatus according to the present embodiment. FIG. 4 is a top view (a view seen in the direction of the arrow A in FIG. 3) showing the elastic member fixing apparatus according to the present embodiment. FIG. 5 is a side view (a view seen in the direction of the arrow B in FIG. 3) showing the elastic member fixing apparatus according to the present embodiment.

As shown in FIGS. 3 to 5, the elastic member fixing apparatus 100 swings the elastic member 6' forming the leg gather 6 in the cross direction CD at a predetermined cycle so as to arrange the elastic member 6' between the second web 7B and the third web 7C. That is, the elastic member fixing apparatus 100 arranges the elastic member 6' in a curved state between the second web 7B and the third web 7C to form the leg gather 6 (the front leg gather 6*a* and the back leg gather 6*b*).

The elastic member fixing apparatus 100 includes at least a web feeding mechanism (unillustrated), a gather feeding mechanism (unillustrated), an adhesive applying mechanism 110, a swinging guide mechanism 120 (guide arm portion), and a press roller mechanism 130.

(3-1) Web Feeding Mechanism

The web feeding mechanism sequentially feeds a web from a jumbo roll. Specifically, the web feeding mechanism has an upper web feeding mechanism which sequentially feeds the third web 7C from a web jumbo roll 7C' and a lower web feeding mechanism which sequentially feeds the second web 7B from a second web jumbo roll 7B'.

The upper web feeding mechanism and the lower web feeding mechanism sequentially feed the second web 7B and the third web 7C to the press roller mechanism 130 through rollers 140A and 140B which rotate around rotation shafts (unillustrated) provided along the cross direction CD.

(3-2) Gather Feeding Mechanism

The gather feeding mechanism sequentially feeds the elastic member 6' forming the leg gather 6 from a jumbo roll. Specifically, the gather feeding mechanism has a front gather feeding mechanism which sequentially feeds the elastic member 6*a*' forming the front leg gather 6*a* from a jumbo roll (unillustrated) and a back gather feeding mechanism which sequentially feeds the elastic member 6*b*' forming the back leg gather 6*b* from a jumbo roll (unillustrated).

The front gather feeding mechanism and the back gather feeding mechanism sequentially feed the leg gather 6 to the press roller mechanism 130 through feed rollers 150A and 150B which rotate around the rotation shafts (unillustrated) provided along the cross direction CD and line-dividing rollers 151A and 151B which divide the elastic member 6a' and the elastic member 6b'.

(3-3) Adhesive Applying Mechanism

The adhesive applying mechanism is a spray-type device for applying an adhesive (for example, a hot-melt adhesive) onto a web. Specifically, the adhesive applying mechanism 110 has an upper adhesive applying mechanism 110A which applies an adhesive onto the third web 7C and a lower adhesive applying mechanism 110B which applies an adhesive onto the second web 7B.

Note that the upper adhesive applying mechanism 110A applies an adhesive onto a surface of the third web 7C except the center portion thereof. On the other hand, the lower adhesive applying mechanism 110B applies an adhesive onto an entire surface of the second web 7B.

(3-4) Shaking Guide Mechanism

The swinging guide mechanism 120 swings the elastic member 6' forming the leg gather 6 in the cross direction CD at a predetermined cycle. The swinging guide mechanism 120 has a first swinging guide mechanism 200A which swings the elastic member 6a' forming the front leg gather 6a and a second swinging guide mechanism 200B which swings the elastic member 6b' forming the back leg gather 6b. The swinging guide mechanism 120 will be described later in detail.

(3-5) Press Roller Mechanism

The press roller mechanism 130 presses the second web 7B and the third web 7C with the elastic member 6' being held between the second web 7B and the third web 7C. Specifically, the press roller mechanism 130 has an upper press roller 130A which comes in contact with the third web 7C and a lower press roller 130B which comes in contact with the second web 7B.

The upper press roller 130A rotates around the rotation shaft 131A provided along the cross direction CD. Similarly, the lower press roller 130B rotates around the rotation shaft 131B provided along the cross direction CD. The elastic member 6' is guided by the swinging guide mechanism 120 to a position where the upper press roller 130A and the lower press roller 130B come closest to each other.

(4) Configuration of Shaking Guide Mechanism

Next, the configuration of the swinging guide mechanism 120 which is a characteristic of the present invention will be described by referring to FIGS. 3 to 5.

The first swinging guide mechanism 200A and the second swinging guide mechanism 200B basically have similar configurations, except that arm members 22 to be described later have different lengths. For this reason, the first swinging guide mechanism 200A and the second swinging guide mechanism 200B are described together as the swinging guide mechanism 120.

As shown in FIGS. 3 to 5, the swinging guide mechanism 120 has a motor 210 with a rotation shaft 211, an arm member 220 which guides the elastic member 6' to a predetermined position in the cross direction CD between the second web 7B and the third web 7C, the rotation shaft 211, and a base 221 of the arm member 220.

(4-1) Motor

The motor 210 is formed of a servomotor which is operated by a controller in which a program is inputted. This program is capable of causing the elastic member 6' to have a predetermined extension magnification and arranging the elastic member 6' in a desired layout according to a conveyance speed (V1) of the web.

The program operating the motor 210 of the first swinging guide mechanism 200A is different from the program operating the motor 210 of the second swinging guide mechanism 200B. That is, the predetermined extension magnification and the layout in the front leg gather 6a are different from the predetermined extension magnification and the layout in the back leg gather 6b.

The motor 210 is attached to a base plate 213 through a bracket 212 (see, FIG. 4). In the base plate 213, the motor 210 is movable in the cross direction CD if needed. When D1 denotes a distance to the press roller mechanism 130 from the base plate 213 equipped with the motor 210 of the first swinging guide mechanism 200A, and D2 denotes a distance to the press roller mechanism 130 from the base plate 213 equipped with the motor 210 of the second swinging guide mechanism 200B, the distances D1 and D2 are different from each other.

(4-2) Arm Member

The arm member 220 forms a tapered plate shape from the base 222 to the tip end portion 222. It is preferable that the arm member 220 be horizontally arranged (see, FIG. 5).

The arm member 220 is formed by using a metal steel plate. For example, the arm member 220 is formed by using a stainless steel plate.

The tip end portion 222 of the arm member 220 is folded towards an opposite side of the arm member 220 from the side on which the motor 210 is positioned. The tip end portion 222 of the arm member 220 has an insertion hole 223 formed therein, the leg gather 6 inserted into the insertion hole 223.

In the present embodiment, the first swinging guide mechanism 200A and the second swinging guide mechanism 200B are different in length of the arm members 220. The length L2 of the arm member 220 of the second swinging guide mechanism 200B is longer than the length L1 of the arm member 220 of the first swinging guide mechanism 200A. On the other hand, the distance from the press roller mechanism 130 to the tip end portion 222 of the first swinging guide mechanism 200A is the same as distance from the press roller mechanism 130 to the tip end portion 222 of the second swinging guide mechanism 200B. For this reason, the relationship between the above-described distance D1 and distance D2 is D2>D1.

For example, the length L1 of the arm member 220 of the first swinging guide mechanism 200A is 450 mm (see, FIGS. 5 to 7). On the other hand, the length L2 of the arm member 220 of the second swinging guide mechanism 200B is 600 mm (see, FIGS. 5 to 7).

Note that the length of the arm member 220 means here a length form the tip end portion 222 of the arm member 220 to the rotation shaft of the arm member 220.

The weight of the arm member 220 of the first swinging guide mechanism 200A is 300 g. On the other hand, the weight of the arm member 220 of the second swinging guide mechanism 200B is 400 g.

The amplitude SW1 of the tip end portion 222 of the arm member 220 of the first swinging guide mechanism 200A along the cross direction CD is 200 mm (see FIG. 4). On the other hand, the amplitude SW2 of the tip end portion 222 of the arm member 220 of the second swinging guide mechanism 200B along the cross direction CD is 350 mm (see FIG. 4).

(5) Operation of Elastic Member Fixing Apparatus (5-1) Overall Operation of Elastic Member Fixing Apparatus Next, the operation of the elastic member fixing apparatus according to the present embodiment will be described by referring to FIGS. 3 to 5.

The third web 7C is fed from the third web jumbo roll 7C' by the upper web feeding mechanism and the moving direction thereof is changed by the roller 140A. Onto a surface of the third web 7C whose moving direction is changed which faces to the second web 7B, an adhesive material is applied by the upper adhesive applying mechanism 110A. At this time, the upper adhesive applying mechanism 110A applies an adhesive onto the surface of the third web 7C except the center portion thereof. The third web 7C onto which the adhesive is applied is supplied between the upper press roller 130A and the lower press roller 130B from above.

Similarly, the second web 7B is fed from the second web jumbo roll 7B' by the lower web feeding mechanism and the moving direction thereof is changed by the roller 140B. Onto the surface of the second web 7B whose moving direction is changed which faces to the third web 7C, an adhesive is applied by the lower adhesive applying mechanism 110B. The second web 7B onto which the adhesive is applied is supplied between the upper press roller 130A and the lower press roller 130B from below.

The elastic member 6a' is fed from the jumbo roll (unillustrated) by the front gather feeding mechanism and is turned the moving direction thereof by the feed roller 150A. The elastic member 6a' turned by the feed roller 150A is divided by the line-dividing roller 151A. The divided elastic member 6a' is swung by the first swinging guide mechanism 200A in the cross direction CD at a predetermined cycle. Accordingly, the elastic member 6a' is arranged in a curved shape between the second web 7B and the third web 7C to form the front leg gather 6a.

Similarly, the elastic member 6b' is fed from the jumbo roll (unillustrated) by the back gather feeding mechanism and is turned the moving direction thereof by the feed roller 150B. The elastic member 6b' turned by the feed roller 150B is divided by the line-dividing roller 151B. The divided elastic member 6b' is swung by the second swinging guide mechanism 200B in the cross direction CD at a predetermined cycle. Accordingly, the elastic member 6b' is arranged in a curved shape between the second web 7B and the third web 7C to form the back leg gather 6b.

The elastic member 6a' and the elastic member 6b' are pressed by the upper press roller 130A and the lower press roller 130B in a state of being held between the second web 7B and the third web 7C onto which an adhesive is applied. For this reason, the elastic member 6a' and the elastic member 6b' are adhered between the second web 7B and the third web 7C in a state of being swung by the swinging guide mechanism 120, so that the above-described large ring portion 6C is formed. On the other hand, even when the elastic member 6a' and the elastic member 6b' are arranged between the second web 7B and the third web 7C, the small ring portion 6d is formed with the generation of resilience in the elastic member 6a' and the elastic member 6b', since the adhesive is not applied to the center portion of the third web 7C.

(5-2) Detailed Operation of Shaking Guide Mechanism

The operation of the swinging guide mechanism 120 will be described in detail by referring to FIGS. 4 and 6. The first swinging guide mechanism 200A and the second swinging guide mechanism 200B are similarly controlled. Therefore, the description will be given by using the first swinging guide mechanism 200A and the elastic member 6a' arranged by the first swinging guide mechanism 200A.

In FIG. 4, the shaking guide mechanism 120 has the tip end portion 222 from which the elastic member 6a' is fed. By using the arm member 220 guiding the elastic member 6a', the tip end portion 222 is alternately moved in a first direction Da and in a second direction Db, the first direction Da directing from the center portion of the second web 7B (third web 7C) being conveyed in the conveyance direction MD to a first end portion 7a in the cross direction CD, and the second direction Db directing from the center portion of the second web 7B (third web 7C) to a second end portion 7b which is an end portion opposite to the first end portion. Accordingly, the elastic member 6a' is brought into contact between the second web 7B and the third web 7C to be arranged in a gather waveform (predetermined waveform).

In FIG. 4, the center line GL shows the center line of the gather waveform in the cross direction CD. In the present embodiment, an amplitude of the elastic member 6a' on the web in the second direction Db from the center line GL has a shorter cycle than that in the first direction Da.

The moving center ML of the tip end portion 222 is offset towards a direction having the shorter cycle of the amplitude, that is, to the second direction Db from the center line GL.

In the present embodiment, the tip end portion 222 forms a feeding portion and the arm member 220 forms a guiding portion. In addition, the conveyance direction MD forms a predetermined direction.

Figure 6:
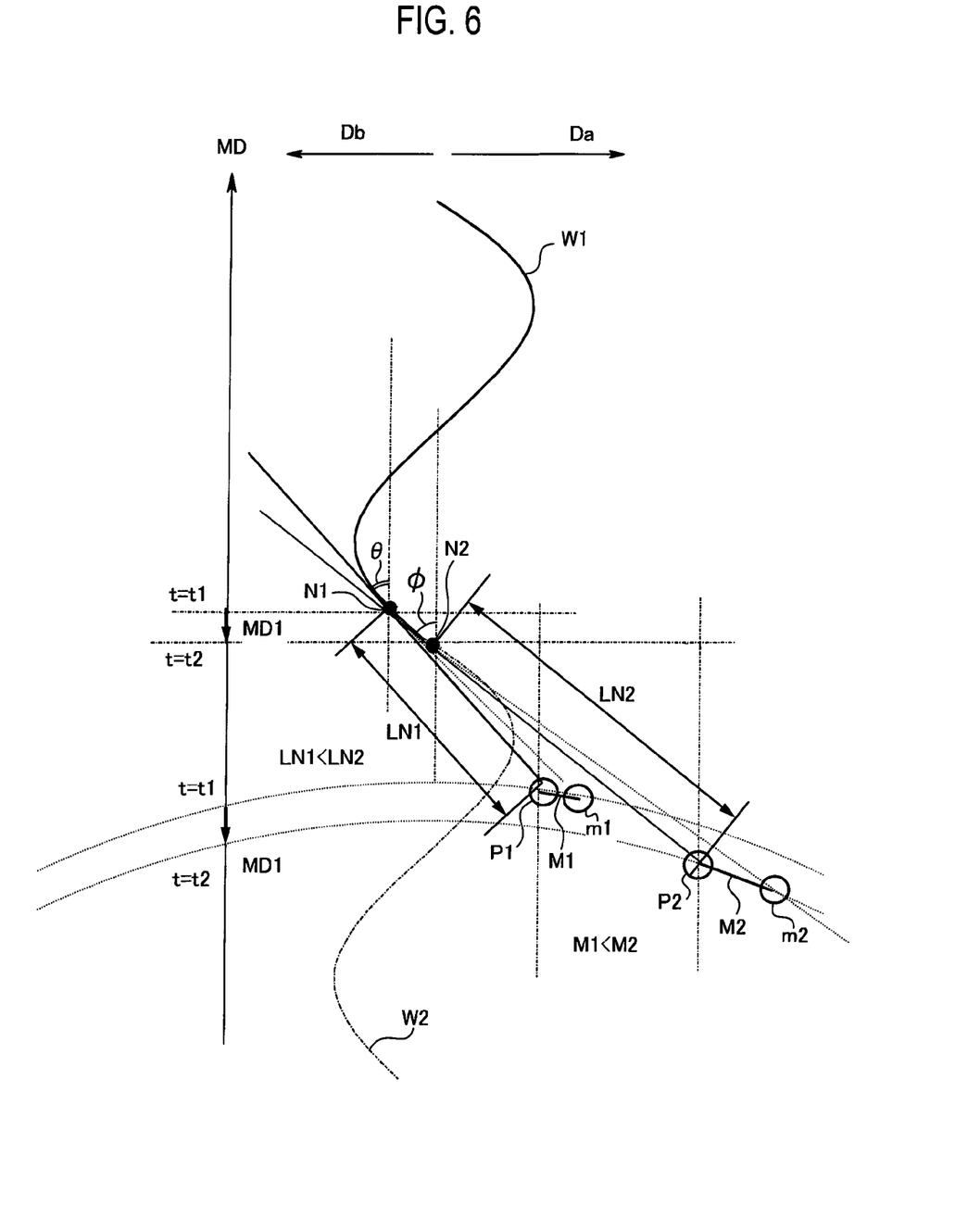
FIG. 6 is a schematic view showing how a front leg gather is arranged in the top view (the view seen in the direction of the arrow A in FIG. 3) shown in FIG. 4.

FIG. 6 is a schematic view for illustrating the movements of the elastic member 6a' arranged on the web and the tip end portion 222 which arranges the elastic member 6a' in the top view (a view seen from the direction of the arrow A in FIG. 3) shown in FIG. 4. The waveform shown in FIG. 6 expresses the waveform of the elastic member 6a' arranged between the second web 7B and the third web 7C and corresponds to the gather waveform of the front leg gather 6a shown in FIG. 4. The solid line portion W1 expresses the waveform of the elastic member 6a' which has already been arranged between the second web 7B and the third web 7C. The broken line portion W2 shows a designed position where the elastic member 6a' is to be arranged.

In the preset embodiment, in the planar view of the composite web 7, a nip point N1 is a position in which the elastic member 6a' is brought into contact with the second web 7B and the third web 7C at time t1. The tip end portion 222 is at least located at a feeding position P1 on the tangent at the nip point N1. At this time, a distance between the tip end portion 222 (that is, the feeding position P1) and the nip point N1 is expressed by a feeding distance LN1.

In general, when the tip end portion 222 is arranged in the feeding position P1 on the tangent to the gather waveform at the nip point N1, the elastic member 6a' can be arranged along the gather waveform. However, in the present embodiment, when the tip end portion 222 is moving in the first direction Da, the tip end portion 222 is arranged in a marginal position m1 which is closer to the first end portion 7a than the feeding position P1 on the tangent to the gather waveform at the nip point N1. Similarly, when moving along the second direction Db, the tip end portion 222 is also arranged in a marginal position which is closer to the second end portion 7b than a feeding position (unillustrated) on the tangent to the gather waveform at the nip point.

In FIG. 6, a nip point N2 is a position in which the elastic member 6a' is brought into contact with the second web 7B and the third web 7C at time t2. The nip point moves by the distance MD1 in the conveyance direction MD from time t1. Here, the directions of the arrows MD1 show the moving directions of the nip point and the tip end portion 222 (feeding position) in relation to the second web 7B and the third web 7C. The tip end portion 222 is at least located at a feeding position P2 on the tangent to the gather waveform at the nip point N2.

Here, an angle φ between the tangent to the gather waveform at the nip point N2 and the conveyance direction MD becomes the largest. That is, the nip point N2 is equal to an inflection point in the curved line showing the gather waveform. In the present embodiment, when the nip point exceeds the position where the angle between the conveyance direction MD and the tangent to the gather waveform becomes the largest (that is, at the nip point N2), the distance (feeding distance LN2) between the tip end portion 222 and the nip point becomes the largest.

That is, when the nip point exceeds the position (that is, at the nip point N2) where the angle between the conveyance direction MD and the tangent to the gather waveform becomes the largest, the feeding distance LN2 is larger than the feeding distance LN1.

When moving in the first direction Da, the tip end portion 222 is arranged in a marginal position m2 which is closer to the first end portion 7a than the feeding position P2 on the tangent to the gather waveform at the nip point N2. Similarly, when moving along the second direction Db, the tip end portion 222 is also arranged in the marginal position which is closer to the second end portion 7b than the feeding position (unillustrated) on the tangent to the gather waveform at the nip point.

In addition, in the present embodiment, a distance M between the position on the tangent and the marginal position of the nip point gradually becomes larger as the nip point moves from the position where the tangent to the gather waveform at the nip point is parallel to the conveyance direction MD, to the position where the angle between the tangent and the conveyance direction MD is largest. That is, in FIG. 6, the marginal distance M1<the marginal distance M2.

In contrast, a distance M between the position on the tangent to the gather waveform at the nip point and the marginal position gradually becomes smaller (unillustrated) as the nip point moves, from the position where the angle between the tangent to the gather waveform at the nip point and the conveyance direction MD is largest, to the position where the tangent is parallel to the conveyance direction MD.

In the present embodiment, it is preferable that the trajectory made along the movement of the tip end portion 222 be a curved line projecting in at least the conveyance direction MD. Specifically, in the present embodiment, the tip end portion 222 is arranged in an arm having the rotational shaft in a predetermined position in relation to the web (gather waveform). That is, the tip end portion draws the arc-shaped trajectory which crosses the conveyance direction MD.

Specifically, in the present embodiment, the swinging guide mechanism 120 is a so-called swing arm swinging unit, which includes the motor 210 having the rotational shaft 211, the arm member 220 guiding the elastic member 6a' to a predetermined position between the second web 7B and the third web 7C in the cross direction CD, the rotational shaft 211, and the base 221 of the arm member 220.

The tip end portion 222 from which the elastic member 6a' is fed is provided at the tip end of the arm member 220. The arm member 220 is connected with the motor 210 having the rotational shaft 211. Accordingly, the feeding position P1 which is the position of the tip end portion 222 and the marginal position m1 are arranged on an arc at time t=t1, the arc having its center at the rotational shaft 21 and having the length of the arm member 220 1 as a radius. Similarly, the feeding position P2 and the marginal position m2 are also arranged on an arc at time t=t2, the arc having its center at the rotational shaft 211 and having the length of the arm member 220 as a radius.

In the present embodiment, as shown in FIG. 4, an amplitude of the elastic member 6a' on the web to the second end portion 7b from the center line GL of the gather waveform in the cross direction CD has a shorter cycle than that to the first end portion 7a and the center of the movement of the tip end portion 222 is offset towards the curvature of the short cycle of the amplitude from the center line GL.

Furthermore, it is preferable that the ratio W/L of the amplitude W of the elastic member 6a' on the composite web 7 to the first direction Da or the second direction Db and the length L of the arm member 220 be between 0.25 and 0.70, both inclusive.

In addition, in the present embodiment, the waveform made of the elastic member arranged by the first swinging guide mechanism 200A and the waveform made of the elastic member arranged by the second swinging guide mechanism 200B are different from each other. Moreover, the length of the arm member 220 provided in the first swinging guide mechanism 200A and the length of the arm member 220 provided in the second swinging guide mechanism 200B are different from each other.

In the present embodiment, as described above, the absorbent article 1 is a wearing-type diaper, and the gather waveform in which the angle between the conveyance direction MD and the tangent to the gather waveform becomes the largest corresponds to an inguinal portion in the leg circumferential region of the diaper.

Specifically, as shown in FIG. 4, the gather waveform in which the elastic member 6a' is arranged by the first swinging guide mechanism 200A corresponds to the waveform of the front leg gather 6a. The region Sk shown in FIG. 4 corresponds to the portion where the angle between the conveyance direction MD and the tangent to the gather waveform becomes the largest. This region Sk corresponds to the inguinal portion of the wearer when the wearer puts on the diaper.

(6) Advantages and Effects

According to the elastic member fixing apparatus 100, in the planar view of the composite web 7, the distance (feeding distance) in the cross direction between the tip end portion 222 and the nip point is larger when the nip point exceeds the position where the angle between the conveyance direction MD and the tangent to the gather waveform becomes the largest.

That is, in the planar view of the composite web 7, the tip end portion 222 is arranged at a longer distance when the nip point exceeds the position where the angle between the conveyance direction MD and the tangent to the gather waveform becomes the largest. The elastic member 6a' is stretched by the tip end portion 222 to a distance more than designed, and thereafter, contracts to come closer to the web, and then comes in contact with the web. Therefore, the elastic member 6a' becomes easy to be arranged in a gather waveform.

Accordingly, according to the elastic member fixing apparatus 100, without requiring precise profile designing, the filiform elastic member 6a' can be easily arranged in a desired position on the web, which is being conveyed at high speed, along the predetermined gather waveform.

In general, when the elastic member is arranged in the gather waveform on the web, in terms of the layout of the apparatus, it is not realistic that the feeding position of the elastic member is brought into contact with the nip point at which the elastic member comes in contact with the web so as to accord the nip point with the feeding position of the elastic member from the feeding position. For this reason, a constant distance is provided between the nip point and the feeding position of the elastic member 6a'.

When the elastic member is to be arranged accurately along the gather waveform, at least the feeding position of the elastic member 6 has to always be arranged on an extension of the tangent to the gather waveform at the nip point.

In addition, when the distance from the feeding position of the elastic member to the nip point is long, even if the feeding position is not accurately arranged on the tangent to the gather waveform at the nip point, a range in which the elastic member can be arranged along the gather waveform is wide.

In the planar view of the composite web 7, when the nip point exceeds the position where the angle between the conveyance direction MD and the tangent to the gather waveform becomes the largest, the distance between the feeding position of the elastic member and the nip point becomes larger. Therefore, the elastic member fixing apparatus 100 can have a wider tolerance range.

Accordingly, according to the elastic member fixing apparatus 100, without requiring precise profile designing, the filiform elastic member 6a' can be easily arranged in a desired position on the web, which is being conveyed at high speed, along the predetermined gather waveform.

In the elastic member fixing apparatus 100, when the tip end portion 222, which is the feeding position of the elastic member 6a, is moving in the first direction Da, the tip end portion 222 is arranged in the marginal position m1 which is closer to the first end portion 7a than the tangent to the gather waveform at the nip point. In addition, when the tip end portion 222 is moving in the second direction Db, the tip end portion 222 is arranged in the marginal position which is closer to the second end portion 7b than the tangent to the gather waveform at the nip point.

Furthermore, the distance M between the position on the tangent to the gather waveform and the marginal position m1 at the nip point gradually becomes larger, as the nip point moves, from the position where the tangent is parallel to the conveyance direction MD, to the position where the angle between the tangent and the conveyance direction MD is largest. In addition, the distance to the position on the tangent to the gather waveform at the nip point becomes gradually smaller as the nip point moves, from the position where the angel between the tangent and the conveyance direction MD is largest, to the position where the tangent is parallel to the conveyance direction MD.

In this manner, the distance from the feeding position of the elastic member 6a' to the nip point can be set to be large in a vicinity of the position where the angle between the tangent and the conveyance direction MD becomes the largest. Therefore, the elastic member fixing apparatus 100 can have a wider tolerance range.

Accordingly, according to the elastic member fixing apparatus 100, without requiring precise profile designing, the filiform elastic member 6a' can be easily arranged in a desired position on the web, which is being conveyed at high speed, along the predetermined gather waveform.

In the elastic member fixing apparatus 100, an amplitude of the elastic member 6a' on the web in the second direction Db from the center line GL of the gather waveform (predetermined waveform) in the cross direction CD has a shorter cycle than that in the first direction Da and the center ML of the movement of the tip end portion 222 is offset towards a direction having the shorter cycle of the amplitude from the center line GL.

For this reason, deviation in the moving amounts of the tip end portion 222 to the first direction and the second direction can be reduced. Accordingly, the feeding position of the elastic member 6a' can more precisely track the gather waveform.

In the present embodiment, the trajectory made along the movement of the tip end portion 222 is a curved line projecting in at least the conveyance direction MD, so that the tip end portion 222 provided at the tip end of the arm member 220 moves on the curved line projecting in the conveyance direction MD. This causes a difference in distance between the tip end portion 222 and the nip point in the conveyance direction MD in addition to the distance therebetween in the cross direction CD. Therefore, the distance (feeding distance) from the feeding position of the elastic member 6a' to the nip point can be extended in the conveyance direction MD. Thus, the tolerance range can be further widened.

Accordingly, without requiring precise profile designing, the filiform elastic member 6a' can be easily arranged in a desired position on the web, which is being conveyed at high speed, along the predetermined gather waveform.

In the present embodiment, the swinging guide mechanism 120 includes the motor 210 having the rotational shaft 211, the arm member 220 guiding the elastic member 6a' to a predetermined position in the cross direction CD between the second web 7B and the third web 7C, the rotational shaft 211, and the base 221 of the arm member 220.

As described above, when the arm member 220 rotates, the tip end portion 222 provided in the tip end of the arm member 220 draws an arc-shaped trajectory. For this reason, on the both ends of the arc, a difference in distance between the feeding position and the nip point is also made in the conveyance direction MD in addition to the distance therebetween in the cross direction CD. Therefore, the distance (feeding distance) from the feeding position of the elastic member 6a' to the nip point can be extended in the conveyance direction MD. Thus, the tolerance range can be further widened.

Accordingly, without requiring precise profile designing, the filiform elastic member 6a' can be easily arranged in a desired position on the web, which is being conveyed at high speed, along the predetermined gather waveform.

In the present embodiment, a ratio W/L of the amplitude W of the elastic member on the web to the first direction Da or the second direction Db and the length L of the arm member 220 is set to be between 0.25 and 0.70 both inclusive. Accordingly, the distance (feeding distance) from the feeding position to the nip point can be properly set and the elastic member 6a' can be arranged along the gather waveform without requiring precise profile designing.

In the present embodiment, the swinging guide mechanism 120 includes one pair of the first swinging guide mechanism 200A and the second swinging guide mechanism 200A, and the waveform in which the elastic member 6a' is arranged by the first swinging guide mechanism 200A and the waveform in which the elastic member 6a' is arranged by the second swinging guide mechanism 200B are different waveforms. In addition, the length of the arm member provided in the first swinging guide mechanism 200A and the length of the arm member provided in the second swinging guide mechanism 200B are different from each other.

With this configuration, multiple elastic members can be respectively arranged along different gather waveforms on one web which is conveyed in the conveyance direction MD at a conveyance speed V1.

In the present embodiment, the absorbent article 1 is a wearing-type diaper, and the gather waveform in which the angle between the conveyance direction MD and the tangent to the gather waveform becomes the largest corresponds to the inguinal portion in the leg circumference regions of the diaper. The region corresponding to the inguinal portion is the most important portion, which determines whether or not the product is comfortable to put on.

The elastic member fixing apparatus 100 can have a wider tolerance range because the distance from the feeding position to the nip point can be set to be longer when the elastic member 6a' is arranged in the position where the angle between the tangent and the conveyance direction MD becomes the largest, that is, in the region Sk corresponding to the inguinal portion.

Accordingly, without requiring precise profile designing, the elastic member 6a' can be accurately arranged in the position corresponding to the inguinal portion in which accuracy of the product is most demanded.

(7) Other Embodiments

As described above, the content of the present invention has been disclosed by using the embodiment of the present invention. However, it should not be understood that the description and drawings which constitute one part of this disclosure limit the present invention. From this disclosure, various alternative embodiments, examples, and operational techniques will be apparent for a person skilled in the art.

For example, the embodiment of the present invention can be modified as follows. Specifically, the manufacturing method of an absorbent article and the elastic member fixing apparatus are not limitedly applicable to the absorbent article 1 (so-called disposable diaper) provided with the front waistline region 10, the back waistline region 20, the crotch region 30, and the like, but can be applicable to various articles such as disposable gowns for medical use and disposable wears for sports.

In addition, the elastic member, which is a component forming the absorbent article 1, has been described as being formed of an elastic filiform rubber or the like. However, the elastic member is not limited to this and may be formed of a flat rubber, a sheet-like rubber, or the like.

Moreover, the elastic member does not have to be a rubber. For example, the elastic member may be a resilient or elastic fiber such as polyester or polyurethane. The elastic member may be an elastic fiber other than these fibers. Some of these fibers may be used by being stranded.

In addition, the first swinging guide mechanism 200A and the second swinging guide mechanism 200B are described to have the arm members 220 with different lengths from each other. However, the lengths thereof are not limited to this but may be the same length.

In addition, the program operating the motor 210 of the first swinging guide mechanism 200A is described to be different from the program operating the motor 210 of the second swinging guide mechanism 200B. However, the configuration is not limited to this, and the program operating the motor 210 of the first swinging guide mechanism 210 may be the same as the program operating the motor 210 of the second swinging guide mechanism 200B. That is, the predetermined extension magnification or the layout in the front leg gather 6a may be same as the predetermined extension magnification or the layout in the back leg gather 6b.

In addition, the insertion hole 223 into which the leg gather 6 is inserted is described to be formed in the tip end portion 222 of the arm member 220. However, the configuration is not limited to this. The tip end portion 222 only needs to guide the leg gather 6. For example, a U-shaped groove may be formed therein.

In the present embodiment, the swinging guide mechanism 120 is described to include the motor 210 having the rotational shaft 211, the arm member 220 guiding the elastic member 6a' to a predetermined position in the cross direction CD between the second web 7B and the third web 7C, the rotational shaft 211, and the base 221 of the arm member 220. However, it is not limited to the configuration in which the arm member 220 rotates around the rotational shaft.

For example, the guiding unit having the feeding position from which the elastic member 6a' is fed may be a mechanism moving in a movement range regulated by an arc-shaped slide rail, an arc-shaped rib, an arc-shaped cam groove and a cam follower, or the like. Driving means applicable to this case includes, for example, a timing belt, a link joint, an arc-shaped linear servo, or the like.

In this manner, as a matter of course, the present invention includes various embodiments which are not described herein. Accordingly, the technical scope of the present invention is defined only by the particular matters contained in the scope of claims which is appropriate from this disclosure.

What is claimed is:

1. A method of manufacturing an absorbent article having elastic members, said method comprising:
    feeding the elastic members in a machine direction by a guide unit including
        (i) first and second swinging arm members having first and second feeding portions respectively feeding the elastic members, and
        (ii) first and second motors having rotational shafts at bases of the first and second arm members, respectively;
    conveying a web that defines components of at least a part of the absorbent article in the machine direction; and
    moving each of the first and second feeding portions by the respective first and second motors alternately in a first direction and a second direction so that the elastic members are brought into contact with the web and are arranged in first and second predetermined waveforms on the web,
    wherein the first direction is directed from a center portion of the web to a first end portion thereof in a cross direction crossing the machine direction, and the second direction is directed from the first end portion of the web to a second end portion thereof that is opposite to the first end portion in the cross direction, and
    wherein in a planar view of the web and during said moving each of the first and second feeding portions,
        when a nip point at which the respective elastic member comes in contact with the web is at a position in the respective predetermined waveform where an angle between the machine direction and a tangent to the respective predetermined waveform is largest, a distance between the feeding portion and the nip point is largest,
        when moving the feeding portion in the first direction, the feeding portion is moved to a first marginal position located closer to the first end portion than an intersection of (i) the tangent to the respective predetermined waveform at the respective nip point and (ii) a respective arc defined by a swinging action of the respective arm member, and
        when moving the feeding portion in the second direction, the feeding portion is moved to a second marginal position located closer to the second end portion than the intersection of (i) the tangent to the respective predetermined waveform at the respective nip point and (ii) said respective arc,
    wherein
    the first and second predetermined waveforms defined by the first and second arm members respectively are different from each other,
    a length of the first arm member is different from that of the second arm member, and
    a dimension between the base of the first arm member and the nip point corresponding to the first arm member is unequal to that between the base of the second arm member and the nip point corresponding to the second arm member in the machine direction.

2. The method according to claim 1, wherein, in the planar view of the web and during said moving each of the first and second feeding portions, a distance between (a) the intersection of the tangent to the respective predetermined waveform at the respective nip point and said respective arc and (b) the first marginal position becomes gradually larger as the respective nip point moves from a position where the tangent is parallel to the machine direction toward the position where the angle between the tangent and the machine direction is largest.

3. The method according to claim 1, wherein, in the planar view of the web and during said moving each of the first and second feeding portions, a distance between (a) the intersection of the tangent to the respective predetermined waveform at the respective nip point and said respective arc and (b) the second marginal position becomes gradually smaller as the respective nip point moves from the position where the angle between the tangent and the machine direction is largest toward a position where the tangent is parallel to the machine direction.

4. The method according to claim 1, wherein, during said moving each of the first and second feeding portions, an amplitude of the respective elastic member on the web in one of the first and second directions from a center line of the respective predetermined waveform in the cross direction has a shorter cycle than that in the other direction, and a center of movement of the feeding portion is offset from the center line in the direction having the shorter cycle of the amplitude.

5. The method according to claim 1, wherein each of said arcs defined by the swinging action of the first and second arm members projects in at least the machine direction.

6. The method according to claim 1, wherein a ratio W/L of an amplitude W of one of the elastic members on the web in one of the first and second directions and a length L of the respective arm member is between 0.25 and 0.70 both inclusive.

7. The method according to claim 1, wherein, during said moving, an amplitude of movement of the first feeding portion from a center line of the first predetermined waveform to the first end portion in the cross direction is greater than that from the center line of the first predetermined waveform to the second end portion in the cross direction.

8. The method according to claim 7, wherein, during said moving, an amplitude of movement of the second feeding portion from a center line of the second predetermined waveform to the first end portion in the cross direction is less than that that from the center line of the second predetermined waveform to the second end portion in the cross direction.

9. The method according to claim 8, wherein, during said moving, the amplitude of movement of the first feeding portion in the cross direction is less than the amplitude in the cross direction of the second feeding portion.

10. A method of manufacturing an absorbent article having elastic members, said method comprising:

feeding the elastic members in a machine direction by a guide unit including
(i) first and second swinging arm members with first and second feeding portions respectively for feeding the elastic members, and
(ii) first and second motors having rotational shafts at bases of the first and second arm members, respectively;

conveying a web that defines components of at least a part of the absorbent article in the machine direction; and moving each of the first and second feeding portion by the respective first and second motors alternately in a first direction and a second direction so that the elastic members are brought into contact with the web and are arranged in first and second predetermined waveforms on the web, wherein the first direction is directed from a center portion of the web to a first end portion thereof in a cross direction crossing the machine direction, and the second direction is directed from the first end portion of the web to a second end portion thereof that is opposite to the first end portion in the cross direction, and wherein in a planar view of the web and during said moving each of the first and second feeding portions, when moving the feeding portion in the first direction, the feeding portion is moved to a first marginal position located closer to the first end portion than an intersection of (i) the tangent to the respective predetermined waveform at a nip point at which the respective elastic member comes in contact with the web and (ii) a respective arc defined by a swinging action of the respective arm member, and when moving the feeding portion in the second direction, the feeding portion is moved to a second marginal position located closer to the second end portion than the intersection of (i) the tangent to the respective predetermined waveform at a nip point at which the respective elastic member comes in contact with the web and (ii) said respective arc, wherein the first and second predetermined waveforms defined by the first and second arm members respectively are different from each other, a length of the first arm member is different from that of the second aim member, and a dimension between the base of the first arm member and the nip point corresponding to the first arm member is unequal to that between the base of the second arm member and the nip point corresponding to the second arm member in the machine direction.

* * * * *